United States Patent [19]
Lee

[11] Patent Number: 4,494,542
[45] Date of Patent: Jan. 22, 1985

[54] SUTURE CUTTER, EXTRACTOR AND METHOD TO CUT AND REMOVE SUTURES

[76] Inventor: Mary K. Lee, 176 Llydican Ave., Ext., Chatham, Ontario, Canada, N7L 3E8

[21] Appl. No.: 386,004

[22] Filed: Jun. 7, 1982

[30] Foreign Application Priority Data

Mar. 31, 1982 [CA] Canada .................................. 400253

[51] Int. Cl.³ ............................................. A61F 17/32
[52] U.S. Cl. ........................................ 128/305; 7/113
[58] Field of Search ................. 30/124, 329; 433/144, 433/145; 128/304, 305; 7/113, 121, 156, 158

[56] References Cited

U.S. PATENT DOCUMENTS

| 1,044,869 | 11/1912 | Emmenegger | 7/113 |
| 2,029,495 | 2/1936 | Lowe | 128/305 |
| 3,201,869 | 8/1965 | Gambino | 30/329 |
| 3,212,187 | 10/1965 | Benedict | 128/305 |
| 3,624,683 | 11/1971 | Matles | 30/124 |
| 4,384,406 | 5/1983 | Tischlinger | 30/124 |
| 4,384,587 | 5/1983 | Milgrom | 128/304 |

FOREIGN PATENT DOCUMENTS 2815257 10/1979 Fed. Rep. of Germany .......... 7/156

Primary Examiner—John D. Yasko
Assistant Examiner—J. L. Kruter
Attorney, Agent, or Firm—Hauke and Patalidis

[57] ABSTRACT

A surgical cutting instrument that is particularly adapted to lift individual ones of sutures from the skin of a patient and to hold each suture by means of a knot at one end thereof while cutting the suture to free it from the skin. The instrument comprises a longitudinally extended body having a generally straight handle portion at one end and a pair of tines at the other end. Both tines are upturned and are of unequal length with blunt innermost edges defining a narrow slot open at one end to snare the knot of a suture. The tine ends are blunt and rounded, the longer of which is insertable under the suture. A longitudinal sharp, thin cutting edge, which comprises a replaceable steel blade in a polycarbonate plastic embodiment, is disposed along a portion of the outermost edge of the longer tine adjacent the junction of both tines and the body. Rotation of the handle brings the sharp edge into cutting relation with the suture which is then severed and removed by lifting the knotted end held fast between the two tines.

8 Claims, 9 Drawing Figures

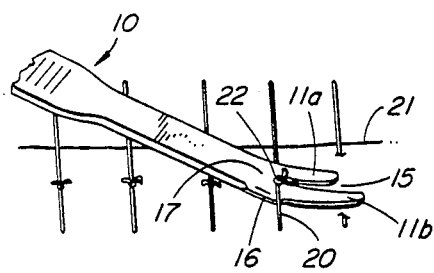
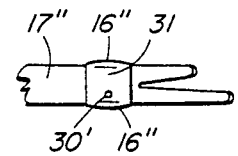
FIG. 4a  FIG. 8
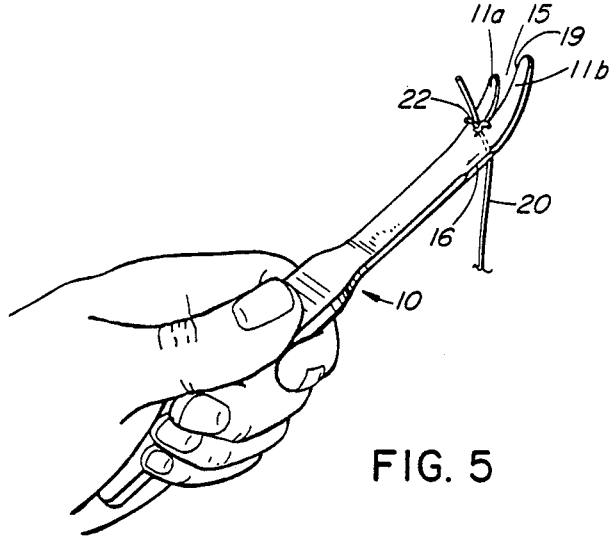
FIG. 5
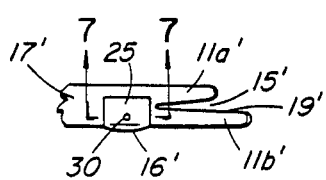
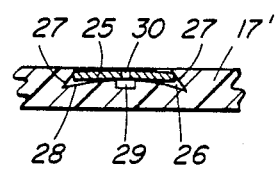
FIG. 6  FIG. 7

SUTURE CUTTER, EXTRACTOR AND METHOD TO CUT AND REMOVE SUTURES

BACKGROUND OF THE INVENTION

The present invention relates to surgical cutting apparatus and more particularly to such apparatus for cutting and extracting a suture.

Suture cutters and extractors of the prior art are known in various forms ranging from conventional scissors and tweezers, each functioning independently of the other, to unitary structures that combine the functional features of both scissors and tweezers. Use of this apparatus requires good finger dexterity in order to effect both suture shearing and gripping actions preparatory to withdrawal of the suture from the skin of a patient. Although such instruments are effective, problems may arise in the course of the tweezing function when attempting to grip an especially fine suture having a very small diameter. Visual acuity is therefore another requirement for effective use of known suture cutters and extractors that include the tweezing function.

SUMMARY OF THE INVENTION

The principal provision of the present invention is a suture cutter and extractor that functions to remove a suture from the skin of a patient without recourse to a tweezing action in order to first grip the suture.

Another provision of the invention is a simple, unitary apparatus not having any moving parts.

Still another provision of the invention is apparatus that may be used ambidextrously for effectively cutting and extracting a suture.

Yet another provision of the invention is a suture cutter and extractor which includes a replaceable blade that is removably attached thereto.

Still another provision of the invention is a suture cutter and extractor which is economical to manufacture and lends itself to simple fabrication from a plastic material.

Still another provision of the invention is a suture cutter and extractor that may be produced and sealed in a sterile package at a sufficiently low cost as to warrant disposal after a single use.

The problems associated with the prior art may be substantially overcome and the foregoing objectives achieved by recourse to the present invention which relates to apparatus for cutting and extracting a suture and which comprises, a pair of tines extending from a longitudinal body, the tines having free ends for insertion under the suture, a slot between the tines open at the free ends to admit and receive the suture when one free end is inserted thereunder and closed at the body to snare and retain a knot in the suture, and a cutting edge disposed along a portion of an outermost side edge of at least one tine adjacent the closed slot end, whereby rotation of the body about the knotted suture engages the edge and suture, severing the latter which is then removed by lifting the knotted end.

DESCRIPTION OF THE DRAWINGS

The invention will now be more particularly described with reference to embodiments thereof shown, by way of example, in the accompanying drawings in which:

FIGS. 4 and 4a are perspective views of the apparatus of FIG. 1 illustrating the manner in which such apparatus is used;

FIG. 5 is a perspective view of the apparatus of FIG. 1 illustrating a suture removed from the skin of a patient;

FIG. 6 is a partial plan view of another embodiment of the present invention;

FIG. 7 is a cross sectional view of FIG. 6 taken along the lines 7—7; and

FIG. 8 is a partial plan view of another embodiment of the present invention.

DESCRIPTION OF THE ILLUSTRATED EMBODIMENTS

Figure 1:
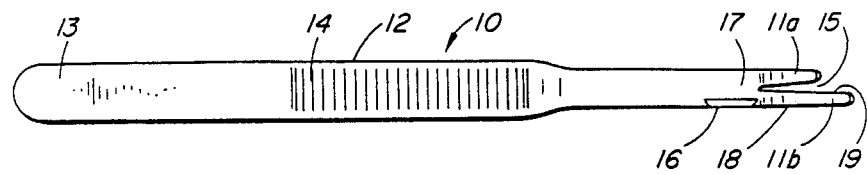
FIG. 1 is a plan view of apparatus for cutting and extracting a suture in accordance with the present invention.

Apparatus 10 for cutting and extracting a suture 20 from a closed wound 21 (FIG. 4) is shown in a plan view in FIG. 1 which depicts a pair of tines 11a and 11b that extend from a longitudinal body 12 having a handle portion 13 at an opposite end, which handle portion includes a gripping surface in the form of a plurality of ridges 14. More particularly, the tines 11a and 11b are curvilinear and curve outwardly upwardly above a plane through the handle portion 13 and the longitudinal axis of the body 12.

The tines 11a and 11b are especially adapted for insertion under the suture 20 and to admit and receive the suture in a slot 15 as the longer tine 11b is inserted under the suture 20. It will be observed that the slot 15 is open at the free ends to freely admit the suture and closed at a neck portion 17 of the body 12 in order to snare and retain a knot 22 as shown in FIGS. 4 and 5.

A cutting edge 16 is disposed along a portion of an outermost side edge of the tine 11b adjacent the closed slot end. As indicated in FIGS. 1 and 2, the cutting edge 16 is an integral part of the apparatus 10, the apparatus being fabricated from fine surgical steel which is especially adapted to receive and retain a very sharp edge.

Figure 4:
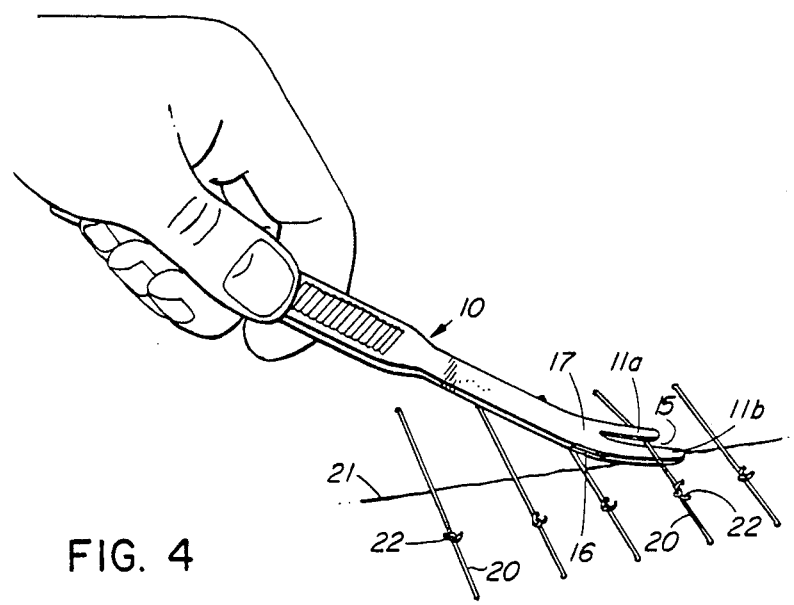

Functionally, the various embodiments of the invention illustrated in the drawings operate in the same manner as typified by the illustrations of FIGS. 4 and 5. Reference to FIG. 4 shows the apparatus 10 with the longer tine 11b inserted under a suture 20, the suture having been admitted to the open end of the slot 15 at the free ends of the tines 11a and 11b. Referring to FIG. 4a, the partial view thereof shows that the suture 20 is subsequently advanced along the slot 15 to the closed end at the neck portion 17. Subsequently, the tines 11a and 11b are drawn up against the knot 22 in order to snare and retain the knot in the slot 15.

Severing the suture 20 is achieved by gently rotating the apparatus 10 about the knot 22 until the cutting edge 16 engages the suture on the other side of the knot. Further rotation severs the suture which is then withdrawn from the wound 21 by lifting the knotted end as illustrated in FIG. 5.

Figure 2:
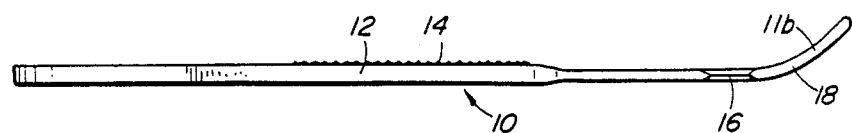
FIG. 2 is a side elevation view of the apparatus of FIG. 1.
Figure 3:
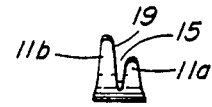
FIG. 3 is an end view of the apparatus of FIG. 2.

The tines 11a and 11b illustrated throughout the figures are shown to be curvilinear, curving outwardly from the long axis of the body 12 as best seen in FIG. 2. Also to be noted is that the tines have rounded free ends to facilitate entry under the suture 20 and blunt edges 18 to avoid injuring a patient. Similar blunt edges, comprising the innermost edges 19 of the tines 11a, and 11b, define the slot 15 wherein it will be noted that the edges 19 converge towards the closed slot end to facilitate knot retention.

The apparatus 10 of FIGS. 1–5 is embodied as a unitary structure including the cutting edge 16. An important prerequisite for this embodiment is that the material from which the apparatus 10 is fabricated be capable of receiving and retaining a very sharp edge as previously described. Other embodiments illustrated in the partial views of FIGS. 6, 7 and 8 are directed to a suture cutter and extractor having a replaceable blade. Apart from the blades, the structures are otherwise similar. Accordingly, similar numerical designations are used to identify similar structural elements.

FIG. 6, for example, illustrates an enlarged partial plan view of a suture cutter and extractor fabricated in accordance with the invention wherein tines 11a' and 11b', joining a neck portion 17', are fabricated from polycarbonate plastic. The enlarged detail of FIG. 6 also shows more clearly the innermost edges 19' which define the slot 15' and the convergence of the edges 19' towards the closed slot end.

The cutting edges 16' in FIG. 6 comprises a replaceable thin blade 25 which is removably attached to the neck portion 17'. The manner of removably attaching the blade 25 is illustrated in FIG. 7 in a partial sectional view showing the blade 25 to be frictionally restrained within a shallow groove 26 that traverses partially a substantially flat region of the neck portion 17' immediately adjacent the closed slot end. FIG. 7 further illustrates the form of the groove 26 which is defined by sloping, undercut side walls 27 and a convexly curviplanar bottom wall 28 having a narrow groove 29 formed therein.

Insertion of the blade 25 within the groove 26 is made from the open end of the groove with the blade 25 being forced into frictional contact with the walls 27 and 28 by means of a probe (not shown) that is insertable in an aperture 30 of the blade. FIG. 7 shows the groove 29 to be in line with the aperture 30 which permits sufficient entry of the probe into the aperture 30 to prevent its slipping out during blade replacement.

The partial plan view of FIG. 8 is similar to that of FIG. 7, the principal differences residing in the length of the shallow groove 26, which completely traverses the width of the neck portion 17'', and in a thin, double-edged replaceable blade 31. Thus, instead of a single cutting edge as illustrated in the preceding embodiments, the embodiment of FIG. 8 includes two cutting edges 16'' to facilitate ambidextrous use. As in the case of the embodiment of FIG. 6, the blade 31 is forced along the groove 26 by means of the probe inserted in the aperture 30'.

It will be apparent to those skilled in the art that the preceding descriptions of the embodiments of the invention may be further varied to meet particular specialized requirements without departing from the true spirit and scope of the invention disclosed. For example, the embodiments of FIGS. 6 and 8 could be fabricated from surgical steel as well as from polycarbonate or some other suitable plastic. Fabrication from surgical steel will result in an embodiment that is sterilizable and therefore suitable for reuse. Conversely, a plastic version is conducive to disposable, single use. Moreover, although the tines are shown as being unequal in length to facilitate insertion under a suture, both tines could be of equal length and, whereas the rate of curvature of both tines is shown to be the same, the rate of curvature of the shorter tine could be made greater than that of the longer tine in a given application. Furthermore, embodiments may be fabricated with the cutting edge on either side to still further facilitate ambidextrous use. Also, predetermined dimensions may be effected for specific suture removal applications such as in the removal of large abdominal sutures, fine sutures of the eye and sutures used in cosmetic surgery. The embodiments described are therefore not to be taken as indicative of the limits of the invention but rather as exemplary structures thereof which is defined by the claims appended hereto.

What I claim is:

1. Apparatus for cutting and extracting a suture, comprising:
    a longitudinally extending body;
    a handle extending from an end of said body;
    a pair of curvilinear tine means extending from the other end of said body, and curving outwardly upwardly above a plane through the handle and the longitudinal axis of said body, the tine means having blunt innermost edges and rounded free ends insertable under the suture, wherein the tine means are of unequal length, the longer tine longer of said tine means being adapted for insertion under the suture, and the tine means having rounded free ends with blunt edges to avoid injuring a patient;
    a slot between the tine means open at the free ends thereof to admit and receive the suture when one of said free ends is inserted thereunder, said slot having converging edges defined by said innermost edges of said tine means and a closed end at the body to snare and retain a knot in said suture; and
    a cutting edge disposed along a portion of an outermost side edge of at least one of said tine means adjacent the closed end of the slot, whereby rotation of the body about the knot in the suture engages the cutting edge with the suture for severing the suture which is then removed by lifting the knot in said suture snared and retained in the closed end of said slot.

2. Apparatus for cutting and extracting a suture, comprising:
    a longitudinally extending body;
    a handle extending from an end of said body;
    a pair of tine means extending from the other end of said body, the tine means having blunt innermost edges and free ends insertable under the suture;
    a slot between the tine means open at the free ends thereof to admit and receive the suture when one of said free ends is inserted thereunder, said slot having converging edges defined by said innermost edges of said tine means and a closed end at the body to snare and retain a knot in said suture;
    a cutting edge disposed along a portion of an outermost side edge of at least one of said tine means adjacent the closed end of the slot, whereby rotation of the body about the knot in the suture engages the cutting edge with the suture for severing the suture which is then removed by lifting the knot in said suture snared and retained in the closed end of said slot;
    said cutting edge comprising a replaceable blade removably attached to a neck portion of the body intermediate the closed slot end and said body, the blade being made from a material especially adapted to receive and retain a sharp edge;

said neck portion comprising side walls defining a substantially flat region immediately adjacent the closed slot end of the tine means; and a shallow groove in one side wall formed transversely of the long axis of the flat region and at least partially thereacross, the groove being adapted to frictionally engage and retain said blade.

3. Apparatus as claimed in claim 2, wherein the shallow groove is defined by sloping, undercut side walls and a convexly curviplanar bottom wall having a narrow groove formed therein.

4. Apparatus as claimed in claim 3, wherein the replaceable blade includes side edges frictionally engageable with the undercut side walls, a bottom surface frictionally engageable with the convex surface of said bottom wall and an aperture adjacent one end of the blade and alignable with said narrow groove.

5. Apparatus as claimed in 4, wherein the shallow groove completely traverses the flat region, the narrow groove partially traverses the flat region and the blade includes a pair of oppositely facing cutting edges disposed along respective portions of the outermost side edges of both tines.

6. Apparatus as claimed in claim 5, wherein said body and tines are fabricated from polycarbonate plastic.

7. A method for cutting free a suture attached to a healed wound, comprising the steps of:
 admitting the suture through an open end of a slot defined by a pair of bifurcated tines extending from a longitudinal body, the tines forming a slot therebetween having edges converging towards a closed end of the slot and having free ends for insertion intermediate the suture and wound and the body having an exterior cutting edge adjacent said closed end of the slot;
 forwardly advancing of body for admitting the suture along the slot between the tines to the closed end of the slot;
 drawing the tines along the suture into abutting relation with a knob therein to snare and retain the knot in the suture in the slot at the closed end thereof; and
 rotating the body about the knot in the suture for engaging the cutting edge with the suture and severing the suture on a side of the knot.

8. A method as claimed in claim 7 comprising the further step of extracting the suture by lifting the knotted end.

* * * * *

UNITED STATES PATENT AND TRADEMARK OFFICE
CERTIFICATE OF CORRECTION

PATENT NO. :   4,494,542
DATED      :   January 22, 1985
INVENTOR(S) :  Mary K. Lee It is certified that error appears in the above-identified patent and that said Letters Patent are hereby corrected as shown below:

Column 3, line 24, change "edges" to --edge--.

Column 5, line 20, after "in" insert --claim--.

Signed and Sealed this

Sixth Day of August 1985

[SEAL]

Attest:

DONALD J. QUIGG

Attesting Officer          Acting Commissioner of Patents and Trademarks